US006137073A

United States Patent [19]

Brown

[11] Patent Number: 6,137,073

[45] Date of Patent: Oct. 24, 2000

[54] ENRICHMENT METHOD FOR RADIOACTIVE ISOTOPES

[76] Inventor: Paul M. Brown, 9510 Sunflower, Boise, Id. 83704

[21] Appl. No.: 09/162,630

[22] Filed: Sep. 28, 1998

[51] Int. Cl.[7] ............................ B01D 5/00; B01D 59/44; A61N 5/00

[52] U.S. Cl. ................................ 204/157.21; 204/157.2; 204/157.22; 250/284; 250/492.1

[58] Field of Search ............................ 204/157.2, 157.21, 204/157.22; 250/284, 492.1

[56] References Cited

U.S. PATENT DOCUMENTS

| | | | |
|---|---|---|---|
| 4,129,481 | 12/1978 | Aubert et al. | 204/1.5 |
| 4,629,600 | 12/1986 | Ishiguro et al. | 376/257 |
| 5,174,873 | 12/1992 | Stevenson et al. | 204/157.2 |
| 5,419,820 | 5/1995 | Horton et al. | 204/157.22 |

FOREIGN PATENT DOCUMENTS

| | | |
|---|---|---|
| 94/17532 | 8/1994 | WIPO . |

*Primary Examiner*—Kathryn Gorgos
*Assistant Examiner*—Edna Wong
*Attorney, Agent, or Firm*—Ken J. Pedersen; Barbara S. Pedersen

[57] ABSTRACT

In the method of this invention, a radioactive isotope, for example, $U^{238}$, is placed within a region. High-energy electrons or high-energy photons in the form of X-rays, gamma rays, or laser excitation are applied to the region. This energy is absorbed by the nucleus of the isotope, placing the nucleus in an excited state. Upon relaxation, the nucleus ejects a neutron, or neutrons, through the gamma-neutron reaction, resulting in a product isotope, namely $U^{235}$.

23 Claims, 3 Drawing Sheets

ENRICHMENT METHOD FOR RADIOACTIVE ISOTOPES

BACKGROUND OF THE INVENTION

1. Field of the Invention

The present invention relates generally to a method for enrichment of radioactive isotopes and more particularly to a method for inducing nuclear reactions that yield enriched radioactive isotopes as a product.

2. Related Art

The present invention relates to a method for photon excitation of nuclear reaction/transmutation processes, to yield enriched radioactive isotopes. More particularly, the present invention relates to a method of radioactive isotope enrichment, which comprises bombarding atoms of the isotope with X-rays, gamma rays or high-energy photons.

U.S. Pat. No. 4,129,481 entitled "Uranium Isotopic Enrichment" issued to Jacques Aubert, et.al., on Dec. 12, 1978, discloses a process of isotopic enrichment of uranium using isotopic exchange between aqueous solutions containing $U^{235}$.

U.S. Pat. No. 5,174,873 entitled "Method of Isotopic Enrichment" issued to Gerald Stevenson, et.al., on Dec. 29, 1992, discloses a method of isotope enrichment using an electron transfer agent to effect a chemical separation of $U^{235}$ present in a reaction mixture.

U.S. Pat. No. 5,419,820 entitled "Process for Producing Enriched Uranium Having a $U^{235}$ Content of at least 4 wt % via Combination of a Gaseous Diffusion Process and an Atomic Vapor Laser Isotope Separation Process to Eliminate Uranium Hexafluoride Tails Storage" issued to James Horton and Howard Hayden, Jr., on May 30, 1995, discloses a process capable of producing enriched uranium using laser isotope separation in a gaseous diffusion mixture containing $U^{235}$.

Each of the above cited U.S. patents describe methods for separating, for example, $U^{235}$ from a mixture of isotopes, yet none of them actually produce more $U^{235}$ than was present to begin with.

An apparatus constructed according to the principles of the present invention does not suffer the performance and efficiency limitations of prior art and produces, for example, $U^{235}$ in samples that previously contained no amount of $U^{235}$.

SUMMARY OF THE INVENTION

It is an object of the present invention to provide a method of producing nuclear reactions that yield enriched radioactive isotopes as a product in a comparatively simple manner.

It is another object of the present invention to provide a method of producing $U^{235}$ by bombarding $U^{236}$ atoms with x-rays, gamma rays, or high energy photons.

This is a process for enrichment of radioactive isotopes or the production of radioactive isotopes through applied nuclear physics. Nuclear reactions, specifically of the gamma, neutron (γ,n) type, also known as the photonuclear reaction, are utilized to accomplish this enrichment. Generally speaking, the target nucleus of the radioisotope to be treated is irradiated by, for example, gamma photons of an energy greater than the binding energy of the neutron in the target nucleus, thereby causing the ejection of said neutron through the (γ,n) reaction.

Other objects, features and advantages of the present invention will become apparent from the following description.

DESCRIPTION OF THE PREFERRED EMBODIMENTS

Figure 1:
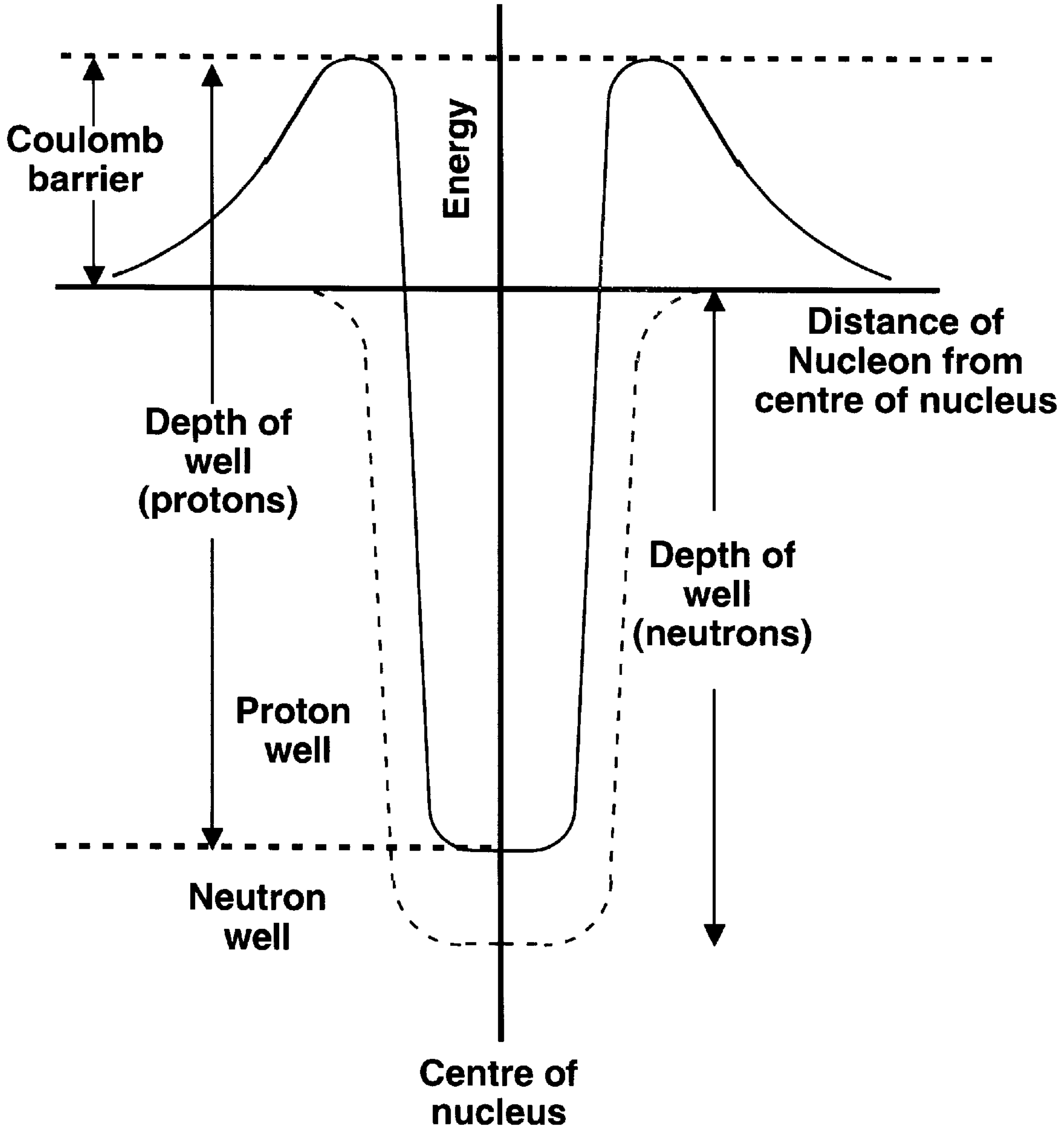
FIG. 1 is a diagramatic representation of the nuclear potential well and the Coulomb barrier.
Figure 2:
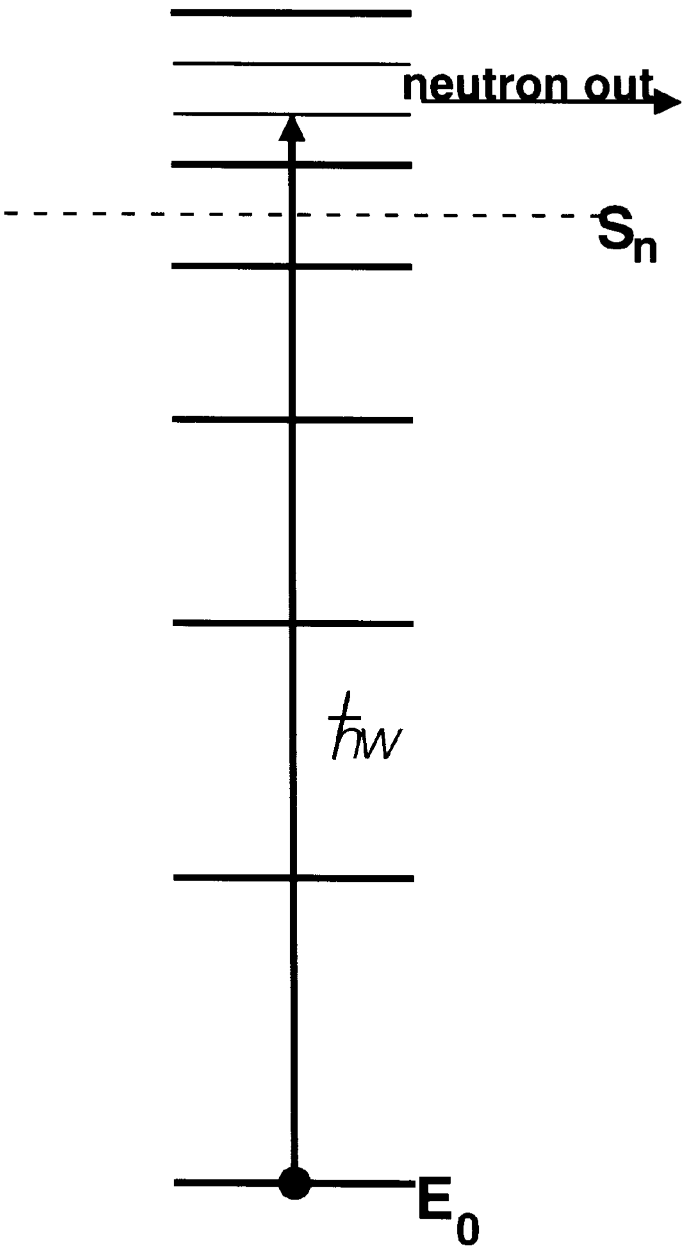
FIG. 2 is a schematic picture of the photonuclear effect with emission of a neutron through the (γ,n) reaction.

In accordance with the present invention, therefore, there is provided a method of producing enriched radioactive isotopes, which method comprises the bombarding of radioactive atoms with high energy, such as x-rays, gamma rays, or high-energy photons (hereinafter "gamma rays"). When the energy of bombarding x-rays, for example, is greater than the binding energy of the neutron to the target nucleus, and the nucleus is excited by this energy absorption from its ground state to an excited state, then the neutron is ejected from the nucleus upon its relaxation from the excited state. This process is called photonuclear enrichment.

Steps involved in the process of photonuclear enrichment are as follows: First, the radioactive isotopes are separated by well known chemical processes. Then, electrons are accelerated in an accelerator, such as a linear accelerator, to impact a high Z target thereby generating x-rays which are used to bombard the nucleus of the isotope to be enriched, knocking a neutron from the nucleus of the atom. A similar process has been used in prior art to produce neutrons. There, typically a stable, non-radioactive atom is subjected to bombardment, and a neutron ejected from the nucleus. The resulting atom without the neutron is then radioactive waste and the neutron is the product. In contrast, according to the method of the present invention, an unstable, radioactive atom, such as $U^{236}$, is subjected to bombardment, and a neutron ejected from the nucleus. The resulting $U^{235}$ is the product and the neutron is a by-product.

Examples of processes according to the current invention are listed in Table I:

TABLE I

| |
|---|
| $U^{236}$ (γ, n) $U^{235}$ |
| $U^{238}$ (γ, 3n) $U^{235}$ |
| $U^{238}$ (γ, 2n) $U^{236}$ (γ, n) $U^{235}$ |
| $Np^{237}$ (γ, 2n)→$Np^{235}$ -e-$^{-}$→$U^{235}$ |
| $Pu^{238}$ (γ, 2n) $Pu^{236}$ (γ, n) $Pu^{235}$ -e-$^{-}$→$Np^{235}$ + $e^{-}$→$U^{235}$ |
| $Pu^{239}$ (γ, 2n) $Pu^{237}$ (γ, 2n) $Pu^{235}$ -e-$^{-}$→$Np^{235}$ + $e^{-}$→$U^{235}$ |
| $Pu^{238}$ (γ, 3n) $Pu^{235}$ -e-$^{-}$→$Np^{235}$ -e-$^{-}$→$U^{235}$ |
| $Pu^{239}$ (γ, 4n) $Pu^{235}$ -e-$^{-}$→$Np^{235}$ -e-$^{-}$→$U^{235}$ |
| $Pu^{239}$ (γ, α) $U^{235}$ |

It has been shown that atomic nuclei are disintegrated by high energy photons; a process called photodisintegration. The best known gamma, neutron reaction is the photodisintegration of the deuteron, $$_1H^2+\gamma\rightarrow {}_1p^1+{}_0n^1$$

If the Q of a reaction is negative, kinetic energy is converted to mass in an endothermic reaction (a negative Q value means that kinetic energy must be brought into the nucleus to make the reaction proceed). The reaction cannot proceed until the photon brings in enough energy to satisfy conservation of energy. This means that the cross section for a gamma, neutron reaction is 0 until the energy is at least equal to Q. The energy of the projectile of which the reaction first has a non-zero cross section is called the threshold energy for the reaction. The threshold of the reaction is that energy of the gamma ray which is just sufficient to break the proton-neutron bond; i.e., the gamma ray must deliver an energy equal to or greater than the binding energy of the nucleon.

The reactions of gamma rays with the nucleus itself (not with its Coulomb field) are scattering; nuclear photoeffect (ejection of neutron, proton, or alpha particle); and photo-fission (for heavy elements). Ejection of a neutron is generally the most probable process because it is not affected by the Coulomb barrier.

With reference to FIG. 1; throughout the central region of the nucleus a nucleon experiences on an average little change in the forces to which the other nucleons subject it, but towards the boundaries it experiences a net attractive force pulling it back towards the center. The same thing would happen if the nucleon moved inside a potential energy well, the potential energy being constant at the center of the well and rising at the walls.

For some purposes it is possible to assume that the nucleus can be represented by such a well, and it turns out that a well about 40 MeV deep and of about the same diameter as the nucleus itself has suitable properties.

For protons, the well is surrounded by a rim. This is because a proton approaching the nucleus is repelled electrostatically, until the moment when it actually touches the nuclear surface. Once it makes contact, it is attracted and falls into the well. The rim is known as the Coulomb barrier. Its height is given by the energy required to bring the proton up to the nuclear surface, i.e., by $Ze^2/R$ (Z=atomic number, e=electronic charge, R=nuclear radius). For heavy nuclei such as uranium the barrier is about 10 MeV high. In the general case of an ion of charge+ze (atomic number times electronic charge) and radius r (nuclear radius) incident on the nucleus the height of the barrier is $Zze^2/(R+r)$.

The concept of the nuclear potential well can be applied both to particles entering or leaving the nucleus, as they do in nuclear reactions, and to nucleons inside the nucleus.

Consideration of the movement of nucleons inside the potential well leads to the shell model of the nucleus. It is assumed that the nucleons move independently inside the well and that their movements are quantized like those of the electrons in the atom. It proves remarkedly successful in accounting for properties of individual nuclei, in both their ground state and excited states. It is particularly successful with odd-A nuclides, in which there is a single unpaired nucleon.

The core excitation model of the nucleus is a model involving electromagnetic properties of the nucleus or the weak-coupling model. This is a model devised for the description of low lying states of odd-A nuclei, which tries to relate such properties to those of the odd particle and the even—even core.

It is important to note that, formulated in this way, there is no assumption about the mechanism which leads to the various core-states. These could be collective vibrations, or single particle excitations, or quasi-particle excitations, or anything else. The essential ingredient that goes into this model is the assumption of a weak coupling between the odd particle and the rest of the nucleus. Weak, that is, in comparison with the interactions involved in the core itself.

Figure 3:
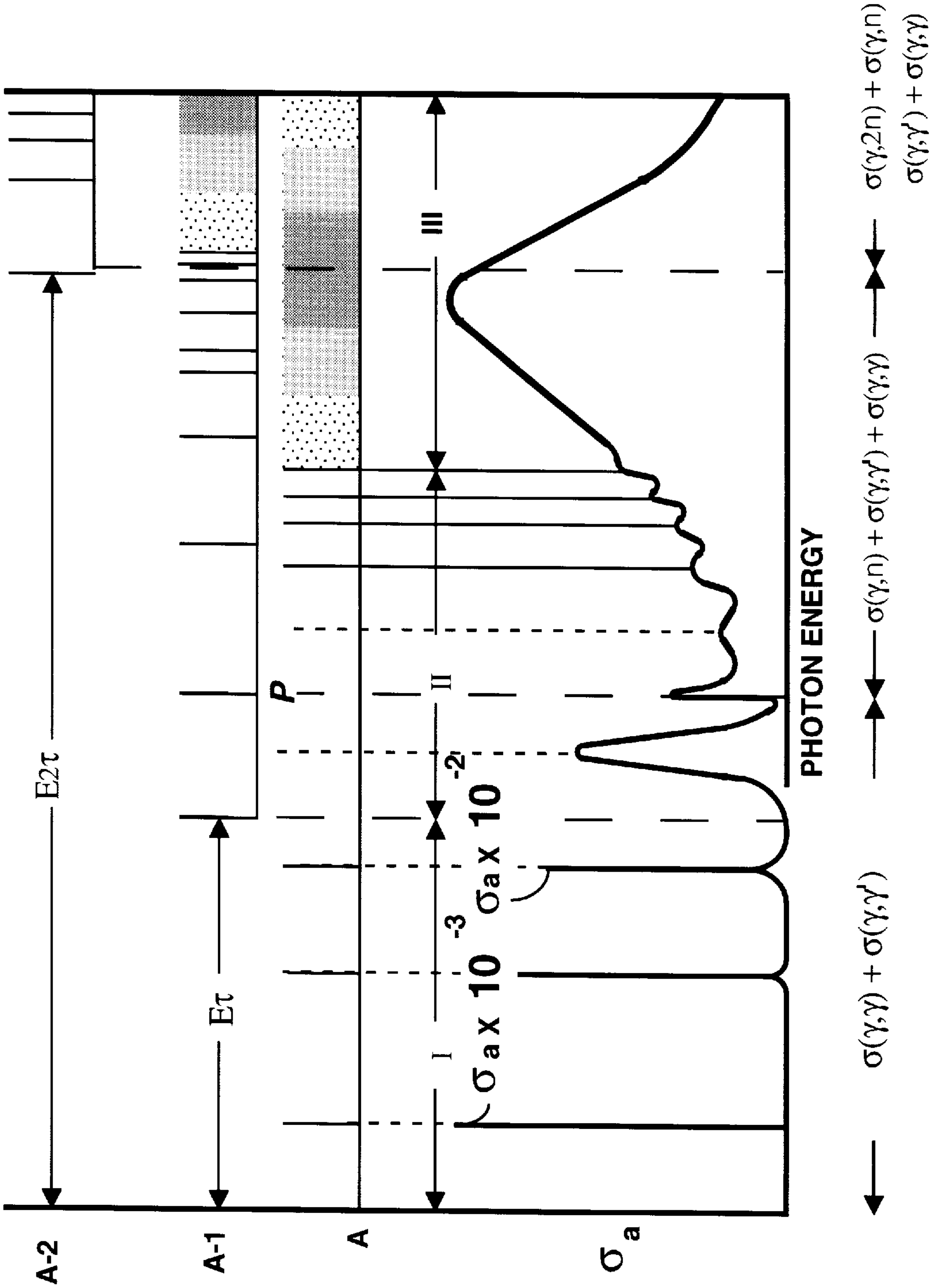
FIG. 3 is the photon absorption cross-section for an idealized nucleus.

With reference to FIG. 3, region I is that part of the energy scale below the particle thresholds where absorption is into discrete energy levels. Region II is the energy range above the binding energy where structure may still exist in the absorption cross-section. In region III the absorption cross section is smooth. The processes that can take place are indicated along abscissa; α(γ, n) here stands for the cross section for nuclear emission. The energy levels in the nucleus A, A-1, and A-2 are illustrated at the top of the diagram. The binding energies for one and two particles are designated by $E_T$ and $E_{2T}$The level $P_1$ in A-1 represents a parent of the ground state of nucleus A. There is indeed an extensive analogy between the kinetics of radioactive decay, and kinetics in a constant flux of nuclear photons, and the equations concerned are closely similar.

If the target species A is radioactive, then both nuclear reaction and decay contribute to its disappearance.

Reactions between nuclei and low- and medium-energy photons are dominated by what is known as a giant resonance: in all nuclei the excitation function for photon absorption (not just for a specific reaction) goes through a broad maximum a few million electron volts wide.

This giant-resonance absorption is ascribed to the excitation of dipole vibrations of all the protons against all the neutrons in the nucleus, the protons and neutrons separately behaving as compressible fluids. This model makes some fairly simple predictions about the magnitude and A-dependence of the resonance that are quite well borne out by the experimental data The energy of the dipole resonance is so low that mostly rather simple processes-such as (yγ, n), (γ, p), (γ, 2n), and photofission reactions-take place in the giant-resonance region. The competition between these processes is governed by the usual statistical considerations of compound-nucleus de-excitation, so that neutron emission usually dominates.

For the common low-energy reactions, the changes in Z and A for the target nucleus are as shown in Table II:

TABLE II

| | A − 3 | A − 2 | A − 1 | A | A + 1 | A + 2 | A + 3 |
|---|---|---|---|---|---|---|---|
| Z + 2 | | | | | | α, 2n | α, n |
| Z + 1 | | | | p, n | p, γ | | α, p |
| | | | | d, 2n | d, n | | |
| Z | | | n, 2n | n, n | n, γ | | |
| | | | γ, n | p, p etc. | d, p | | |
| Z − 1 | p, α | d, α | γ, p | n, p | | | |
| Z − 2 | n, α | | | | | | |

The emission of single nucleons in (γ, n) and (γ, p) reactions requires an excitation energy of about 8 MeV. In this region the levels overlap and an exact energy match is not needed for absorption of the γ-ray.

The application of the method of this invention is available without development of new technologies. It should be noted that application of this method would provide a boost to the nuclear power industry by providing a cheap, effective method for producing reactor fuel.

There is also the neutron flux produced as a by-product of the enrichment process. This neutron flux may be used for activation as well as neutron enrichment, such as in Table III:

TABLE III $$U^{234} + n \rightarrow U^{235}$$
$$U^{238} + n \rightarrow U^{239} - e^{-} \rightarrow Pu^{239}$$
$$Th^{232} + n \rightarrow Th^{233} - e^{-} \rightarrow Pa^{233} - e^{-} \rightarrow U^{233}$$

TABLE IV

| Nuclide | Reaction | G, N Threshold (MeV) | G, 2N Threshold (MeV) | Max Energy (MeV) | Maximum Cross Section (mB) | Integrated Cross Section (mB) |
|---|---|---|---|---|---|---|
| U-238 | G, ABS | 6.1 | 11.3 | 13.5 | 450 | 2950 |
| U-238 | G, XN | 6.1 | 11.3 | 14.0 | 1221 | 7465 |
| U-238 | G, 2N | 6.1 | 11.3 | 14.29 | 280 | 1132 |
| U-236 | G, N | — | — | 11.4 | 290 | 1256 |
| Pu-239 | G, ABS | 5.7 | 11.5 | 12.0 | 450 | 2970 |
| Pu-239 | G, XN | 5.7 | 11.5 | 13.84 | 1674 | 9806 |
| Pu-239 | G, 2N | 5.7 | 12.7 | 13.35 | 64 | 153 |
| Np-237 | G, 2N | 6.6 | 12.3 | 14.3 | 130 | 349 |

REACTIONS LEGEND:

| | |
|---|---|
| G, ABS | Total photoabsorption cross section |
| G, N | Single neutron cross section |
| G, 2N | Double neutron cross section |
| G, XN | Neutron yield cross section |

Although this invention has been described above with reference to particular means, materials and embodiments, it is to be understood that the invention is not limited to these disclosed particulars, but extends to all equivalents within the scope of the following claims.

What I claim is:

1. A method of radioactive isotopic enrichment comprising:

providing a radioactive isotope, and irradiating said radioactive isotope with gamma rays to emit a nucleon from said isotope, thereby producing a product isotope of reduced atomic mass.

2. The method of isotope enrichment of claim 1 wherein said isotope is U-238.

3. The method of isotope enrichment of claim 1 wherein said isotope is U-236.

4. The method of isotope enrichment of claim 1 wherein said isotope is Np-237.

5. The method of isotope enrichment of claim 1 wherein said isotope is Pu-238.

6. The method of isotope enrichment of claim 1 wherein said isotope is Pu-239.

7. The method of isotope enrichment of claim 1 wherein said reaction is the gamma, neutron nuclear reaction.

8. The method of isotope enrichment of claim 1 wherein said reaction is the gamma, 2 neutron nuclear reaction.

9. The method of isotope enrichment of claim 1 wherein said reaction is the gamma, X neutron—where X is 1–4 nuclear reaction.

10. The method of isotope enrichment of claim 1 wherein said reaction is the gamma, alpha nuclear reaction.

11. The method of isotope enrichment of claim 1 wherein said gamma rays have a minimum energy equal to or greater than the nucleon binding energy.

12. The method of isotope enrichment of claim 1 wherein said isotope of reduced atomic mass is U-235.

13. The method of isotope enrichment of claim 1 wherein said isotope of reduced atomic mass is Np-235.

14. The method of isotope enrichment of claim 1 wherein said isotope of reduced atomic mass is $Pu^{235}$.

15. The method of isotope enrichment of claim 1 wherein said product isotope is an intermediate.

16. The method of isotope enrichment as in claim 15 wherein said intermediate is Np-235.

17. The method of isotope enrichment as in claim 15 wherein said intermediate is $Pu^{235}$.

18. A method of producing U-235 comprising:

providing a radioactive isotope selected from the group consisting of U-238, U-236, Np-237, Pu-238 and Pu-239, and irradiating said radioactive isotope with gamma rays to cause a reaction and to emit a nucleon from said isotope, thereby producing U-235.

19. The method of producing U-235 as in claim 18 wherein said reaction is the gamma, neutron nuclear reaction.

20. The method of producing U-235 as in claim 18 wherein said reaction is the gamma, 2 neutron nuclear reaction.

21. The method of producing $U^{235}$ as in claim 18 wherein said reaction is the gamma, X neutron—where X is 1–4 nuclear reaction.

22. The method of producing $U^{235}$ as in claim 18 wherein said reaction is the gamma, alpha nuclear reaction.

23. The method of producing U-235 as in claim 18 wherein said gamma rays have a minimum energy equal to or greater than the nucleon binding energy.

* * * * *